United States Patent [19]

Hasegawa et al.

[11] Patent Number: 5,368,639

[45] Date of Patent: Nov. 29, 1994

[54] ORGANOSILICON-TREATED PIGMENT, PROCESS FOR PRODUCTION THEREOF, AND COSMETIC MADE THEREWITH

[75] Inventors: Yukio Hasegawa, Kasukabe; Ryota Miyoshi, Yono; Isao Imai, Kuki, all of Japan

[73] Assignee: Miyoshi Kasei Co., Ltd., Urawa, Japan

[21] Appl. No.: 903,225

[22] Filed: Jun. 25, 1992

[30] Foreign Application Priority Data

Jun. 26, 1991 [JP] Japan .................. 3-250164

[51] Int. Cl.$^5$ .................. C04B 14/04; A61K 7/00
[52] U.S. Cl. .................. 106/490; 106/481; 106/2; 106/18.12; 106/287.1; 106/806; 424/78.03
[58] Field of Search .............. 106/490, 481, 2, 18.12, 106/287.1, 806; 424/78.03

[56] References Cited

U.S. PATENT DOCUMENTS

| | | | |
|---|---|---|---|
| 3,377,311 | 4/1968 | Roch | 523/213 |
| 3,388,073 | 6/1968 | Domba | 106/490 |
| 3,929,718 | 12/1975 | Kratel et al. | 523/213 |
| 4,151,154 | 4/1979 | Berger | 523/203 |
| 4,263,051 | 4/1981 | Crawford et al. | 106/490 |
| 4,529,774 | 7/1985 | Evans et al. | 106/490 |

OTHER PUBLICATIONS

Patent Abstracts of Japan, vol. 16, No. 63 (C-911) [506], abstract for JP 3-258866, published Feb. 18, 1992.

*Primary Examiner*—Karl Group
*Assistant Examiner*—Scott L. Hertzog
*Attorney, Agent, or Firm*—Armstrong, Westerman, Hattori, McLeland & Naughton

[57] ABSTRACT

Disclosed herein are (1) an organosilicon-treated pigment which comprises a pigment or extender pigment and a linear reactive alkylpolysiloxane having in the molecule amino groups, imino groups, halogen atoms, hydroxyl groups, or alkoxyl groups, which is adhered in an oriented mode to the surface of the pigment or extender pigment by heat treatment, (2) a process for producing said treated pigment, and (3) a cosmetic made with said treated pigment. The organosilicon-treated pigment is characterized by silicone firmly adhered to the surface of a pigment or extender pigment, freedom from residual hydrogen, very smooth feel, good adhesion to the skin, and ability to permit the color pigment of fine particle size to spread well. The treated pigment finds use as a component of high-quality cosmetics such as powder foundation, liquid foundation, rouge, and eye shadow.

3 Claims, No Drawings

ORGANOSILICON-TREATED PIGMENT, PROCESS FOR PRODUCTION THEREOF, AND COSMETIC MADE THEREWITH

BACKGROUND OF THE INVENTION

1. Field of the Invention

The present invention relates to an organosilicon-treated pigment, a process for production thereof, and a cosmetic made therewith, and more particularly, to a new pigment and extender pigment which are smooth, superior in adhesion and spreadability, and completely free of residual hydrogen, a process for production of said pigment, and a cosmetic made with said pigment.

2. Description of the Prior Art

An organosilicon compound, especially methylhydrogenpolysiloxane, finds use as a surface treatment agent for pigments and extender pigments. The surface-treated pigments and pigment extenders are now in general use for lasting makeup and two-way type cosmetics because of their high water repellency.

The ordinary method for surface treatment does not permit the reactive Si-H groups of the silicone molecule to undergo complete reaction. The percent conversion is such that 30–60% of hydrogen remains unreacted. This holds true of methylhydrogenpolysiloxane. Its crosslinking reaction does not proceed completely on account of steric hindrance, with hydrogen remaining unreacted. Pigments or extender pigments with such residual hydrogen give off gaseous hydrogen (which presents a danger of explosion) upon processing into cosmetics under alkaline or acidic conditions. Moreover, the resulting cosmetics expand their containers or cloud the compact glass as time goes by.

Those pigments vulnerable to heat, such as yellow oxide, Prussian blue, and Red 202 (Lithol Rubine BCA), may be treated at a low temperature by the aid of a catalyst. A disadvantage of this method is that the catalyst remains unreacted.

There has been proposed a process for treatment with methylhydrogenpolysiloxane to improve the percent conversion by addition of an acid substance or an alkali metal hydroxide. A disadvantage of this process is that methylhydrogenpolysiloxane undergoes crosslinking polymerization which gives rise to silicone resin of reticulate three-dimensional structure. This silicone resin forms particles, which in turn bring about the strong coagulation of pigment particles. Therefore, the resulting treated pigment feels rough and is very poor in spreadability and adhesion to the skin.

Another improvement is by mechanochemical treatment that employs a jet atomizer. The percent conversion of methylhydrogenpolysiloxane by this method is still as low as 20–70%, depending on the kind of pigment for treatment. Hence, the above-mentioned problem associated with residual hydrogen remains unsolved. Moreover, the mechanochemical treatment resorting to crushing deforms the particles of pigment or extender pigment. This is disadvantageous to a pigment or extender pigment composed of flaky or needlelike particles. In addition, the mechanochemical treatment requires special facilities which are not suitable for production of a variety of products in small quantities.

SUMMARY OF THE INVENTION

The present invention was completed to solve the above-mentioned problem. It is an object of the present invention to provide an organosilicon-treated pigment which is characterized by smooth feel, good adhesion to the skin, no coagulation and residual hydrogen, and ability to provide a very high saturation and tone when mixed with said color pigment. It is another object of the present invention to provide an organosilicon-treated pigment which can be produced in a simple manner from any heat-vulnerable pigment at a low temperature without the aid of catalyst using the existing equipment unmodified. It is further another object of the present invention to provide a process for the production of said treated pigment and a cosmetic which contains said treated pigment.

The gist of the present invention resides in an organosilicon-treated pigment which comprises a pigment or extender pigment and a linear reactive alkylpolysiloxane having in the molecule amino groups, imino groups, halogen atoms, hydroxyl groups, or alkoxyl groups, which is adhered in an oriented mode to the surface of the pigment or extender pigment by heat treatment.

DETAILED DESCRIPTION OF THE INVENTION

According to the present invention, the organosilicon-treated pigment is made with a linear reactive alkylpolysiloxane which has at the terminal of the molecular chain such reactive groups as amino group ($-NH_2$), imino group ($=NH$), halogen atom (e.g., Cl, Br, and I), hydroxyl group ($-OH$), and alkoxyl group ($-OR$, where R denotes an alkyl group). It should have a degree of polymerization (n) of 7–1000, preferably 20–100.

Examples of the alkylpolysiloxane include dimethylpolysiloxysilazane, $\alpha$-monohydroxysiloxane, $\alpha,\omega$-dihydroxypolydimethylsiloxane, $\alpha$-monoalkoxypolydimethylsiloxane, $\alpha$-dialkoxypolydimethylsiloxane, $\alpha$-trialkoxypolydimethylsiloxane, $\alpha,\omega$-dialkoxypolydimethylsiloxane, $\alpha,\omega$-hexalkoxypolydimethylsiloxane, dimethylpolysiloxy chloride, dimethylpolysiloxy bromide, and dimethylpolysiloxy iodide. Preferred examples are $\alpha$-monoalkoxypolydimethylsiloxane, $\alpha$-dialkoxypolydimethylsiloxane, and $\alpha$-trialkoxypolydimethylsiloxane. They are adhered to the pigment very easily, thereby imparting a smooth feel to the treated pigment. The reactive group in the alkylpolysiloxane may be joined to the silicon atom directly or indirectly through a substituent group.

The pigment or extender pigment in the present invention embraces inorganic pigments (such as titanium oxide, zinc oxide, zirconium oxide, yellow iron oxide, black iron oxide, red iron oxide, ultramarine, Prussion blue, chromium oxide, and chromium hydroxide), iridescent pigments (such as titanium mica and bismuth oxychloride), organic dyestuffs (such as tar dyestuffs and natural dyestuffs), and powder (such as silica beads, plastic (nylon or polyacryl) beads, talc, kaolin, white mica, cericite, other micas, magnesium carbonate, calcium carbonate, aluminum silicate, magnesium silicate, calcium silicate, clay and the like). Desirable of these examples are fine particles or superfine particles (smaller than 1 $\mu$m in diameter) of titanium oxide and color pigments (such as yellow iron oxide, black iron oxide, red iron oxide, ultramarine, Prussian blue, chromium oxide, chromium hydroxide, tar dyestuffs and the like). They are superior in adhesion and spreadability.

According to the present invention, the organosilicon compound (or the linear reactive alkylpolysiloxane)

should be used in an amount of 0.1–30 wt %, preferably 2–5 wt %, of the pigment or extender pigment to be treated, depending on its particle diameter and specific surface area.

According to the present invention, the organosilicon-treated pigment is produced by mixing a linear reactive alkylpolysiloxane specified above, an organic solvent which dissolves said polysiloxane, and a pigment or extender pigment, and drying the mixture by heating.

A proper organic solvent should be selected in consideration of its flash point and ignition point and the surface activity and heat stability of the pigment or extender pigment for surface treatment. Preferred examples of the organic solvent include ethers, ketones, halogenated hydrocarbons, aliphatic hydrocarbons, and alcohols and mixture thereof or with other solvents such as water. The organic solvent should be used in an amount of 1–50 wt % to the pigment or extender pigment.

The mixing of the reactive alkylpolysiloxane, organic solvent, and pigment or extender pigment may be accomplished by putting them together into an ordinary mixer or by spraying the reactive alkylpolysiloxane onto a mixture of the organic solvent and pigment or extender pigment. The heating of the mixture should be carried out in an adequate manner in consideration of the heat resistance of the pigment or extender pigment and the kind of the organic solvent used.

The present invention also provides a cosmetic which contains the organosilicon-treated pigment mentioned above. The term "cosmetic" comprehends powder foundation, liquid foundation, rouge, eye shadow, and the like.

As mentioned above, the organosilicon-treated pigment of the present invention is one which comprises a pigment or extender pigment and a linear reactive alkylpolysiloxane which is adhered in an oriented mode to the surface of the pigment or extender pigment by heat treatment. The linear reactive alkylpolysiloxane readily adheres to and reacts with a variety of powder as the pigment, whereas it does not undergo crosslinking polymerization leading to the three-dimensional structure. Therefore, it permits the surface treatment of heat-vulnerable pigments under mild conditions without the aid of catalyst. The resulting treated pigment has a smooth feel and is superior in adhesion to the skin and free from coagulation. Although the surface treatment may be accompanied by release of ammonia or hydrogen chloride, these compounds are completely removed upon heating, leaving no residue. The treated pigment with outstanding properties as mentioned above is used to make a cosmetic having good adhesion. Particularly, it imparts a highly saturated tone to a cosmetic containing the treated-pigment.

EXAMPLES

The invention will be described in more detail with reference to the following examples, in which "parts" means "parts by weight". [Organosilicon-treated pigment]

EXAMPLE 1

100 g of talc (JA-46R made by Asada Seifun Co., Ltd.) and 8 g of benzene were mixed with each other for 5 minutes using a home mixer. The mixture was further mixed with 2 g of dimethylpolysiloxysilazane (n+100) by spraying for 5 minutes. The mixture was dried at 80° C. to remove benzene completely and then heated at 115° C. for 3 hours. Thus there was obtained a treated pigment having a smooth feel and good adhesion.

Comparative Example 1

The same procedure as in Example 1 was repeated except that the dimethylpolysiloxysilazane was replaced by methylhydrogenpolysiloxane. The resulting treated pigment was poor in adhesion notwithstanding its smooth feel.

EXAMPLE 2

The same operation as in Example 1 was performed on 100 g of red iron oxide (made by Morishita Bengara Kogyo Co., Ltd.), 10 g of carbon tetrachloride, and 5 g of dimethylpolysiloxane chloride (n+50). There was obtained a treated pigment having a smooth feel and good adhesion.

Comparative Example 2

The same procedure as in Example 2 was repeated except that the dimethylpolysiloxane chloride was replaced by methylhydrogenpolysiloxane. The resulting treated pigment was poor in both adhesion and feel.

EXAMPLE 3

100 g of titanium oxide (CR-50 made by Ishihara Sangyo Co., Ltd.) and 12 g of chloroform were mixed with each other for 5 minutes using a home mixer. The mixture was further mixed with 5 g of dihydroxydimethylsiloxane (n=100) by spraying for 5 minutes. The mixture was air-dried at 80° C. and then heated at 105° C. for 3 hours. Thus there was obtained a treated pigment having a smooth feel and good adhesion, free from coagulation.

Comparative Example 3

100 g of titanium oxide (CR-50 made by Ishihara Sangyo Co., Ltd.), 2 g of glutamic acid, and 5 g of methylhydrogenpolysiloxane underwent grinding in a pot mill for 8 hours. The treated product was poor in adhesion, with a rough feel.

EXAMPLE 4

100 of calcined mica (having an average particle size of 5 μm), 25 g of a 2:1 mixture of water and isopropyl alcohol, and 3 g of α-trialkoxypolydimethylsiloxane (n=30) were mixed with one another for 5 minutes using a home mixer. The mixture was heated at 115° C. for 6 hours. Thus there was obtained a mica powder having polydimethylsiloxane oriented and adsorbed to the surface thereof. This powder has a much smoother feel than the calcined mica (having an average particle size of 5 μm) surface-treated with methylhydrogenpolysiloxane. In addition, it has a moist feel and yet exhibits strong water repellency.
[Cosmetics]

EXAMPLE 5

A powder foundation of the following formulation was prepared.

| Component 1 | |
|---|---|
| Talc | 35.0 parts |
| Cericite | 20.0 parts |
| Mica powder | 15.0 parts |
| Titanium oxide | 7.0 parts |
| Titanium oxide (fine particle) | 5.0 parts |

| | |
|---|---|
| Yellow iron oxide | 3.5 parts |
| Black iron oxide | 0.5 part |
| Red iron oxide | 2.0 parts |
| Component 2 | |
| Liquid paraffin | 5.0 parts |
| Stearyl alcohol | 3.0 parts |
| Beeswax | 3.0 parts |
| Squalene | 1.0 part |

Component 1, which is a mixture of pigments and extender pigments, was surface-treated with dimethylpolysiloxysilazane by the method of Example 1. The treated pigments were mixed with one another using a Henschel mixer and then ground using an atomizer. The ground product was mixed with Component 2 (which had been heated) using a Henschel mixer and then ground again using an atomizer. The ground product was filled into a cosmetic container to form a desired product (powder foundation).

Comparative Example 4

The same procedure as in Example 5 was repeated except that the dimethylpolysiloxysilazane for surface treatment was replaced by methylhydrogenpolysiloxane.

Comparative Example 5

The same procedure as in Example 5 was repeated except that 100 g of Component 1 (which is a mixture of pigments and extender pigments) underwent grinding in a ball mill for 5 hours, and further underwent grinding together with 5 g of methylhydrogenpolysiloxane for 5 hours.

Three samples of powder foundation obtained in Example 5 and Comparative Examples 4 and 5 were tested for adhesion, color saturation, and water repellency. The results are shown in Table 1. The criteria for rating are as follows:

5: very good
4: slightly good
3: mediocre
2: slightly poor
1: very poor

TABLE 1

| Sample | Spreadability | Adhesion | Saturation | Water repellency |
|---|---|---|---|---|
| Example 5 | 5 | 5 | 5 | 5 |
| Comparative Example 4 | 3 | 3 | 4 | 5 |
| Comparative Example 5 | 2 | 2 | 3 | 5 |

5: very good
4: slightly good
3: mediocre
2: slightly poor
1: very poor

Each of the treated pigments obtained in Example 5 and Comparative Examples 4 and 5 was ground twice or three times using an atomizer, and the ground product was made into a sample of powder foundation. It was tested for spreadability, adhesion, color saturation, and water repellency in the same manner as mentioned above. The results are shown in Table 2 (ground twice) and Table 3 (ground three times).

TABLE 2

| Sample | Spreadability | Adhesion | Saturation | Water repellency |
|---|---|---|---|---|
| Example 5 | 5 | 5 | 5 | 5 |
| Comparative Example 4 | 3 | 3 | 4 | 5 |
| Comparative Example 5 | 2 | 2 | 3 | 4 |

TABLE 3

| Sample | Spreadability | Adhesion | Saturation | Water repellency |
|---|---|---|---|---|
| Example 5 | 5 | 5 | 5 | 5 |
| Comparative Example 4 | 2 | 2 | 5 | 4 |
| Comparative Example 5 | 2 | 2 | 4 | 3 |

It is noted from the foregoing that in the case of conventional silicone treatment the powder foundation improves in color saturation but becomes poor in spreadability, adhesion, and water repellency in proportion to the number of repetitions of crushing by an atomizer, whereas in the case of silicone treatment according to the present invention the powder foundation remains unaffected by the repeated crushing by an atomizer.

EXAMPLE 6

A liquid foundation of the following formulation was prepared.

| | |
|---|---|
| Component A | |
| Cyclomethycon | 12.0 parts |
| Emulsified volatile oil | 2.0 parts |
| Titanium oxide | 9.0 parts |
| Red iron oxide | 0.7 part |
| Yellow iron oxide | 0.2 part |
| Black iron oxide | 3.0 parts |
| Talc | 2.0 parts |
| Component B | |
| Propylparaben | 0.2 part |
| Polyoxyethylene lauryl ether | 0.5 part |
| Component C | |
| Emulsified volatile oil | 18.0 parts |
| Dimethylsilicone (50 cs.) | 3.0 parts |
| Tocopherol acetate | 0.1 part |
| Corn oil | 0.05 part |
| Component D | |
| Methylparaben | 0.2 part |
| Propylene glycol | 8.0 parts |
| Component E | |
| Sodium dehydroacetate | 0.3 part |
| Pantothenyl alcohol | 0.2 part |
| Sodium chloride | 2.0 parts |
| Purified water (to make) | 100.0 parts |

First, Component A, which is a mixture of pigments and extender pigments, was surface-treated with dimethylpolysiloxysilazane (2%) in the same manner as in Example 1. Component A was mixed with Components B and C, which had been melted by heating at 60° C. Components D and E were mixed with each other after melting by heating at 60° C. To the first mixture was slowly added the second one with stirring to effect emulsification. Upon cooling, there was obtained a sample of liquid foundation.

Comparative Example 6

The same procedure as in Example 6 was repeated to prepare a sample of liquid foundation except that the dimethylpolysiloxysilazane for surface treatment was replaced by methylhydrogenpolysiloxane.

The samples of liquid foundation obtained in Example 6 and Comparative Example 6 were stored in polyethylene bottles for 1 month to see if they change with time and they liberate hydrogen. The liberated hydrogen was detected by means of a hydrogen detector tube. The results are shown in Table 4.

TABLE 4

| Sample | Change with time | Hydrogen liberation |
|---|---|---|
| Example 6 | none | none |
| Comparative Example 6 | none | yes |

It is noted from Table 4 that the sample according to the present invention does not liberate hydrogen, whereas the comparative sample treated with a conventional silicone liberates hydrogen. This result suggests that the cosmetic of the present invention is superior in stability and feel to the conventional one.

Each sample of the treated pigments obtained in Example 5 and Comparative Examples 4 and 5 was tested for the dissolution of silicone in chloroform. Test method:

To 20 g of sample (treated pigment) was added 100 ml of chloroform. After stirring for 30 minutes, the dispersion was filtered through a glass filter. The solid was washed twice with 20 ml of chloroform. The filtrate was dried at 100° C. for 10 hours and then at 120° C. for 1 hour, and the amount of the extracted silicone was accurately measured. It was found that the amount of the silicone dissolved in chloroform was 25% in Example 5, 45% in Comparative Example 4, and 38% in Comparative Example 5. The amount of the extracted silicone of the present invention is much less than that of conventional one. This result suggests that silicone is firmly adsorbed to pigment in the case of surface treatment according to the present invention.

As mentioned above, the present invention provides an organosilicon-treated pigment which is characterized by silicone firmly adsorbed to the surface of a pigment or extender pigment, freedom from residual hydrogen, very smooth feel, good adhesion to the skin, and ability to permit the color pigment of fine particle to spread well. The treated pigment having such outstanding properties finds use as a component of high-quality cosmetics such as powder foundation, liquid foundation, rouge, and eye shadow.

What is claimed is:

1. An organosilicon-treated pigment which comprises a pigment or extender pigment treated with a linear reactive alkylpolysiloxane having terminal amino groups, imino groups, halogen atoms, hydroxyl groups, or alkoxyl groups, and having a degree of polymerization of 30–1,000 whereby said alkylpolysiloxane is adhered in an oriented mode to the surface of the pigment or extender pigment.

2. A process for producing an organosilicon-treated pigment, said process comprising mixing a linear reactive alkylpolysiloxane having terminal amino groups, imino groups, halogen atoms, hydroxyl groups, or alkoxyl groups, and having a degree of polymerization of 30–1,000 with an organic solvent capable of dissolving said alkylpolysiloxane and a pigment or extender pigment, and drying the mixture by heating.

3. A cosmetic which comprises an organosilicon-treated pigment as defined in claim 1.

* * * * *

UNITED STATES PATENT AND TRADEMARK OFFICE
CERTIFICATE OF CORRECTION

PATENT NO. :   5,368,639
DATED      :   November 29, 1994
INVENTOR(S):   HASEGAWA et al.

It is certified that error appears in the above-identified patent and that said Letters Patent is hereby corrected as shown below:

On the title page:   Item [30], add --June 8, 1992 [JP] Japan 4-173861--.

Signed and Sealed this

Eleventh Day of April, 1995

Attest:

BRUCE LEHMAN

Attesting Officer        Commissioner of Patents and Trademarks